US011337985B2

(12) United States Patent
Munoz Patino et al.

(10) Patent No.: US 11,337,985 B2
(45) Date of Patent: May 24, 2022

(54) PHARMACEUTICAL COMPOSITION FOR USE IN THE PROPHYLACTIC AND/OR THERAPEUTIC TREATMENT OF L-DOPA-INDUCED DYSKINESIA (71) Applicant: UNIVERSIDADE DE SANTIAGO DE COMPOSTELA, Santiago de Compostela (ES)

(72) Inventors: Ana M. Munoz Patino, Santiago de Compostela (ES); Jose Luis Labandeira Garcia, Santiago de Compostela (ES); Andrea Lopez Lopez, Santiago de Compostela (ES)

(73) Assignee: UNIVERSIDADE DE SANTIAGO DE COMPOSTELA, Santiago de Compostela (ES)

( * ) Notice: Subject to any disclaimer, the term of this patent is extended or adjusted under 35 U.S.C. 154(b) by 0 days.

(21) Appl. No.: 17/406,689

(22) Filed: Aug. 19, 2021

(65) Prior Publication Data
US 2021/0393646 A1  Dec. 23, 2021

Related U.S. Application Data (63) Continuation of application No. PCT/ES2020/070482, filed on Jul. 24, 2020.

(51) Int. Cl.
*A61K 31/551* (2006.01)
*A61P 25/14* (2006.01)
*A61K 31/198* (2006.01)

(52) U.S. Cl.
CPC .......... *A61K 31/551* (2013.01); *A61K 31/198* (2013.01); *A61P 25/14* (2018.01)

(58) Field of Classification Search
None
See application file for complete search history.

(56) References Cited

PUBLICATIONS

Vijayakumar et al. "Drug-Induced Dyskinesia, Part 1: Treatment of Levodopa-Induced Dyskinesia," Drugs (2016) 76:759-777 (Year: 2016).*
Espay et al. "Levodopa-Induced Dyskinesia in Parkinson Disease: Current and Evolving Concepts," Ann Neurol 2018;84:797-811. (Year: 2018).*
Perez-Lloret et al. "Renin-angiotensin system as a potential target for new therapeutic approaches in Parkinson's disease," Expert Opinion on Investigational Drugs, 2017 vol. 26, No. 10, 1163-1173 (Year: 2017).*
Vasant More et al. "Emerging preclinical pharmacological targets for Parkinson's disease," Oncotarget, 2016 vol. 7, No. 20; 29835. (Year: 2016).*
Inan et al. "Behavioural effects of basal ganglia rho-kinase inhibition in the unilateral 6-hydroxydopamine rat model of Parkinson's disease," Metab Brain Dis (2016) 31:849-857. (Year: 2016).*
Naoki Sakai et al., "Parallel Induction of Nitric Oxide and Tetrahydrobiopterin Synthesis by Cytokines in Rat Glial Cells", Journal of Neurochemistry, 1995, pp. 895-902, vol. 65, No. 2.
Timothy Schallert et al., "Intervention Strategies for Degeneration of Dopamine Neurons in Parkinsonism—Optimizing Behavioral Assessment of Outcome", Central Nervous System Diseases, 1999, pp. 131-151.
Hengrui Sun et al., "Rho and ROCK Signaling in VEGF-Induced Microvascular Endothelial Hyperpermeability", 2006, Microcirculation, pp. 237-247, vol. 13.
Yoshio Suzuki et al., "A postmarketing surveillance study of fasudil treatment after aneurysmal subarachnoid hemorrhage", Elsevier, Surgical Neurology, 2007, pp. 126-132, vol. 68.
Asmaa M. Teema et al., "Ibuprofen or piroxicam protects nigral neurons and delays the development of L-dopa induced dyskinesia in rats with experimental Parkinsonism: Influence on angiogenesis*", Elsevier, Neuropharmacology, 2016, pp. 432-450, vol. 107.
S. Walsh et al., "Time-course nigrostriatal neurodegeneration and neuroinflammation in the 6-hydroxydopamine-induced axonal and terminal lesion models of parkinson's desease in the rat", Neuroscience, 2011, pp. 251-261, vol. 175.
Tan Wang et al., "Effect of simvastatin on L-DOPA-induced abnormal involuntary movements of hemiparkinsonian rats", Neurol Sci, 2015, pp. 1397-1402, vol. 36.
Christian Winkler et al., "L-DOPA-Induced Dyskinesia in the Intrastriatal 6-Hydroxydopamine Model of Parkinson's Disease: Relation to Motor and Cellular Parameters of Nigrostriatal Function", Neurobiology of Disease, 2002, pp. 165-186, vol. 10.
Jianhuan Wu et al., "Rho-Kinase Inhibitor, Fasudil, Prevents Neuronal Apoptosis via the Akt Activation and PTEN Inactivation in the Ischemic Penumbra of Rat Brain", Cell Mol Neurobiol, 2012, pp. 1187-1197, vol. 32.
International Search Report of International Application No. PCT/ES/2020/070482, dated Sep. 9, 2020.
C. Warren Olanov et al., A new look at an old friend. Movement Disorders, 2018, pp. 859-866, vol. 33, No. 6.
Begona Villar-Cheda et al., "Involvement of microglial RhoA/Rho-Kinase pathway activation in the dopaminergic neuron death. Role of angiotensin via angiotensin type 1 receptors", Elsevier, Neurobiology of Disease,Apr. 11, 2012, pp. 268-279, vol. 47, No. 2.
Ghanemi Abdelaziz, "Targeting G protein coupled receptor-related pathways as emerging molecular therapies", Saudi Pharmaceutical Journal, Aug. 13, 2013, pp. 115-129, vol. 23, No. 2.
Fahn Stanley, "How Do You Treat Motor Complications in Parkinson's Disease: Medicine, Surgery, or Both?", Annals of Neurology, Dec. 2008, pp. S56-S64, vol. 64, N° 6, Suppl. S.
Rene Gunther et al., "Rho Kinase Inhibition with Fasudil in the SOD1G93A Mouse Model of Amyotrophic Lateral Sclerosis—Symptomatic Treatment Potential after Disease Onset", Frontiers in Pharmacology, Jan. 31, 2017, vol. 8, Article 17.
Renata P. Lerner et al., "Levodopa-induced abnormal involuntary movements correlate with altered permeability of the blood-brain-barrier in the basal ganglia", Nov. 22, 2017, Scientific Reports, vol. 7: 16005.

(Continued)

*Primary Examiner* — Jeffrey S Lundgren
*Assistant Examiner* — Michael J Schmitt
(74) *Attorney, Agent, or Firm* — McBee Moore & Vanik, IP, LLC; Susan E. Shaw McBee (57) ABSTRACT

Pharmaceutical composition for use in the prophylactic and/or therapeutic treatment of dyskinesias induced by L-DOPA. The present invention relates to the pharmaceutical field, more particularly to the use of Rho kinase inhibitors for treating or preventing dyskinesias induced by L-DOPA.

13 Claims, 11 Drawing Sheets

(56) References Cited

PUBLICATIONS

M. Takata et al., "Fasudil, a rho kinase inhibitor, limits motor neuron loss in experimental models of amyotrophic lateral sclerosis", British Journal of Pharmacology, 2013, pp. 341-351, vol. 170.

KM Mair et al.,"Novel interactions between the 5-HT transporter, 5-HT1B receptors and Rho kinase in vivo and in pulmonary fibroblasts", British Journal of Pharmacology, 2008, pp. 606-616, vol. 155.

Natalia Moskal et al., "ROCK inhibitors upregulate the neuroprotective Parkin-mediated mitophagy pathway", Nature Communications, 2020, vol. 11, No. 88.

Ana Munoz et al., "Combined 5-HT1A and 5-HT1B receptor agonists for the treatment of L-DOPA-induced dyskinesia", Brain A Journal of Neurology, 2008, pp. 3380-3394, vol. 131.

Hiromichi Nakabayashi et al., "HA1077, a Rho kinase inhibitor, suppresses glioma-induced angiogenesis by targeting the Rho-ROCK and the mitogen-activated protein kinase kinase/extracellular signal-regulated kinase (MEK/ERK) signal pathways", Cancer Science, Feb. 2011, pp. 393-399, vol. 102, No. 2.

Anju Nohria et al., "Statins inhibit Rho kinase activity in patients with atherosclerosis", Elsevier, Atherosclerosis, 2009, pp. 517-521, vol. 205.

K. Elisabei Ohlin et al., "Vascular endothelial growth factor is upregulated by L-dopa in the parkinsonian brain implications for the development of dyskinesia", Brain a Journal of Neurology, 2011, pp. 1-19.

M. Olsson et al., "Forelimb Akinesia in the Rat Parkinson Model: Differential Effects of Dopamine Agonists and Nigral Transplants as Assessed by a New Stepping Test", The Journal of Neuroscience, May 1995, pp. 2863-2875, vol. 15, No. 5.

J. Rodriguez-Pallares et al., "Mechanism of 6-hydroxydopamine neurotoxicity: the role of NADPH oxidase and microglial activation in 6-hydroxydopamineinduced degeneration of dopaminergic neurons", Journal of Neurochemistry, 2007, pp. 145-156, vol. 103.

Ana I. Rodriguez-Perez et al., "Dopaminergic neuroprotection of hormonal replacement therapy in young and aged menopausal rats: role of the brain angiotensin system", Brain A Journal of Neurology, pp. 124-138, vol. 135.

Ramon Soto-Otero et al., "Autoxidation and Neurotoxicity of 6-Hydroxydopamine in the Presence of Some Antioxidants: Potential Implication in Relation to the Pathogenesis of Parkinson's Disease", Journal of Neurochemistry, 2000, pp. 1605-1613, vol. 74. No. 4.

Hidayuki Takeuchi et al., "Tumor Necrosis Factor- Induces Neurotoxicity via Glutamate Release from Hemichannels of Activated Microglia in an Autocrine Manner*", The Journal of Biological Chemestry, Jul. 28, 2006, pp. 21362-21368, vol. 281, No. 30.

Lars Tatenhorst, PhD et al., "Rho Kinase Inhibition by Fasudil in the Striatal 6-Hydroxydopamine Lesion Mouse Model of Parkinson Disease", Journal of Neuropathology and Experimental Neurology, Jul. 2014, vol. 73, No. 8.

Yuwen Wu et al., "Microglia: Dynamic Mediators of Synapse Development and Plasticity", Trends Immunol., Oct. 2015; pp. 605-613, vol. 36, No. 10.

Zhang SJ, "Study on the Pharmacokinetics of Fasudil, a selective Rho kinase inhibitor", Asian Journal of Pharmacodynamics and Pharmacokinetics, 2009, pp. 221-226, vol. 9, No. 3.

Carlos Barcia et al., "ROCK/Cdc42-mediated microglial motility and gliapse formation lead to phagocytosis of degenerating dopaminergic neurons in vivo", Scientific Reports, Nov. 8, 2012, vol. 2, No. 809.

C. J. Barnum et al., "Exogenous Corticosterone Reduces L-Dopa-induced dyskinesia in the hemi-parkisonian rat: role for interfleukin-1 Beta", Neuroscience, 2008, pp. 30-41, vol. 156.

Laura Boi et al., "Immunomodulatory Drugs Alleviate L-Dopa-Induced Dyskinesia in a Rat Model of Parkinson's Disease", Movement Disorders, 2019, vol. 34, No. 12.

Brad A. Bryan, "RhoA/ROCK signaling is essential for multiple aspects of VEGF-mediated angiogenesis", The FASEB Journal, Sep. 2010, pp. 3186-3195, vol. 24.

M. Angela Cenci et al., "Maladaptive striatal plasticity in L-DOPA-induced dyskinesia", Prog Brain Res., 2010, pp. 209-233, vol. 183.

Alberto J. Espay et al., "Levodopa-induced dyskinesia in Parkinson disease: Current and Evolving Concepts Dyskinesia in Parkinson disease", American Neurological Association, 2018, pp. 1-16, vol. 00, No. 0.

Qing-Fang Gu et al., "Therapeutic effect of Rho kinase inhibitor FSD-C10 in a mouse model of Alzheimer's disease", Experimental and Therapeutic Medicine, 2018, pp. 3929-3938, vol. 16.

Sarah J. Heasman et al., "Multiple roles for RhoA during T cell transendothelial migration", Small GTPases, Landes Bioscience, Nov./Dec. 2010, pp. 174-179, vol. 1, No. 3.

Mien V.Hoang et al., "Rho activity critically and selectively regulates endothelial cell organization during angiogenesis", PNAS, Feb. 17, 2004, pp. 1874-1879, vol. 101, No. 7.

Henk Honing et al., "RhoA activation promotes transendothelial migration of monocytes via ROCK", Journal of Leukocyte Biology, Mar. 2004, pp. 523-528, vol. 75.

Tom Jhonston et al., "Repurposing drugs to treat L-DOPA-induced dyskinesia in Parkinson's disease", Elsevier, Neuropharmacology, 2018, pp. 1-17.

Mei Li et al., "Intravitreal Administration of HA-1077, a ROCK Inhibitor, Improves Retinal Function in a Mouse Model of Huntington Disease", PLOS ONE, Feb. 2013, vol. 8, No. 2.

Paul Lingor et al., "ROCK-ALS: Protocol for a Randomized, Placebo-Controlled, Double-Blind Phase IIa Trial of Safety, Tolerability and Efficacy of the Rho Kinase (ROCK) Inhibitor Fasudil in Amyotrophic Lateral Sclerosis", Frontiers in Neurology, Mar. 2019, vol. 10, Article 293.

Andrea Lopez-Lopez et al., "Rho kinase inhibitor fasudil reduces L-DOPA-induced dyskinesia in a rat model of Parkinson's disease", doi: 10 1111/bph.15275, published Dec. 2020.

Jong-Heon Kim et al., "Microglia-inhibiting activity of Parkinson's disease drug amantadine", Elsevier, Neurobiology of Aging, 2012, pp. 2145-2159, vol. 33.

J. L. Labandeira-Garcia et al., "Time course of striatal changes induced by 6-hydroxydopamine lesion of the nigrostriatal pathway, as studied by combined evaluation of rotational behaviour and striatal Fos expression", Exp Brain Res, 1996, pp. 69-84, vol. 108.

J. L. Labandeira-Garcia et al., "Rho Kinase and Dopaminergic Degeneration: A Promising Therapeutic Target for Parkinson's Disease", The Neuroscientist, 2015, pp. 616-629, vol. 21, No. 6.

Giovanna Mulas et al., "Differential induction of dyskinesia and neuroinflammation by pulsatile versus continuous L-DOPA delivery in the 6-OHDA model of Parkinson's disease", Elsevier, Experimental Neurology, 2016, pp. 83-92, vol. 286.

Ana Munoz et al., "Angiotensin type 1 receptor blockage reduces L-dopa-induced dyskinesia in the 6-OHDA model of Parkinson's disease. Involvement of vascular endothelial growth factor and interleukin-1 Beta", Elsevier, Experimental Neurology, 2014, pp. 720-732, vol. 261.

Fernando Eduardo Padovan-Neto et al., "Effects of prolonged neuronal nitric oxide synthase inhibition on the development and expression of L-DOPA-induced dyskinesia in 6-OHDA-lesioned rats", Elsevier, Neuropharmacology, 2015, pp. 87-99, vol. 89.

Augusta Pisanu et al., "Neuroinflammation in I-DOPA-induced dyskinesia: beyond the immune function", Journal oi Neural Transmission, 2018, pp. 1287-1297, vol. 125.

Ana I. Rodriguez-Perez et al., "Inhibition of Rho kinase mediates the neuroprotective effects of estrogen in the MPTP model of Parkinson's disease", Elasevier, Neurobiology of Disease, 2013, pp. 209-219, vol. 58.

Olivier Defert et al., "Rho kinase inhibitors: a patent review (2014-2016)", Expert Opinion on Therapeutic Patents, pp. 507-515, vol. 27 No. 4.

Eric C. Beattie et al., "Control of Synaptic Strength by Glial TNFalfa", Science, Mar. 22, 2002, pp. 2282-2285, vol. 295.

Ana Borrajo et al., "Inhibition of the microglial response is essential for the neuroprotective effects of Rho-kinase nhibitors on MPTP-induced dopaminergic cell death", Elsevier, Neuropharmacology, 2014, pp. 1-8, vol. 85.

Mariza Bortolanza et al., "Glial activation is associated with L-DOPA induced dyskinesia and blocked by a nitric oxide synthase inhibitor (56) References Cited

PUBLICATIONS in a rat model of Parkinson's disease", Elsevier, Neurobiology of Disease, 2015, pp. 377-387, vol. 73.

Javier Carbajo-Lozoya et al., "Angiotensin II modulates VEGF-driven angiogenesis by opposing effects of type 1 and type 2 receptor stimulation in the microvascular endothelium", Elsevier, Cellular Signalling, 2012, pp. 1261-1269, vol. 24.

Manolo Carta et al., "Role of striatal L-DOPA in the production of dyskinesia in 6-hydroxydopamine lesioned rats", Journal of Neurochemistry, 2006, pp. 1718-1727, vol. 96.

M. Angela Cenci et al., "Animal Models of L-Dopa-Induced Dyskinesia in Parkinson's Disease", Movement Disorders, 2018, pp. 889-899, vol. 33, No. 6.

Alexander Gerhard et al., "In vivo imaging of microglial activation with [11C](R)-PK11195 PET in idiopathic Parkinson's disease", Elsevier, Neurobiology of Disease, 2006, pp. 404-412, vol. 21.

\* cited by examiner

PHARMACEUTICAL COMPOSITION FOR USE IN THE PROPHYLACTIC AND/OR THERAPEUTIC TREATMENT OF L-DOPA-INDUCED DYSKINESIA

CROSS-REFERENCE TO RELATED APPLICATIONS

This is a bypass continuation of International Application No. PCT/ES2020/070482, filed 24 Jul. 2020, which claims priority to Spanish Application No. P201930713, filed 31 Jul. 2019, the content of each of which is incorporated herein by reference in its entirety.

DESCRIPTION

Pharmaceutical composition for use in the prophylactic and/or therapeutic treatment of dyskinesias induced by L-DOPA

FIELD OF THE INVENTION

The present invention relates to the pharmaceutical field, more particularly to the use of Rho kinase inhibitors for treating or preventing dyskinesias induced by L-DOPA.

BACKGROUND

Parkinson's disease (PD) is one of the commonest neurodegenerative diseases in our population. It is mainly characterized by motor symptoms that arise owing to degeneration of the dopaminergic neurons of the substantia nigra, although other systems of neurons are also involved. The usual, and to date the most effective, treatment for this disease consists of administering the dopamine precursor molecule, L-DOPA. This drug proves effective in the initial years, but in the longer term it gives rise to complications and side effects, including dyskinesias in particular.

The dyskinesias induced by L-DOPA consist of abnormal rapid involuntary movements of the choreic type and athetosis, which usually affect the extremities and sometimes the face and neck region. Several forms of dyskinesia have been described, depending on the temporal pattern of expression: peak-dose dyskinesias (coinciding with the highest plasma levels of dopamine), diphasic dyskinesias and off-period dystonia. These complications may become incapacitating, since they greatly reduce the therapeutic effect of L-DOPA, limiting the patients' daily activity. It has been described that after 5 years of treatment about 50% of patients have dyskinesias, while at 10 years the percentage increases to 90% (Olanow C W, Stocchi F. Levodopa: A new look at an old friend. Mov Disord (2018) 33(6):859-866. doi: 10.1002/mds.27216).

The causes involved in the development of dyskinesias are not fully known, although it is known that the glutamatergic system plays an important role. In fact, the drug used at present for combating dyskinesias is amantadine, an NMDA glutamate receptor antagonist. However, this compound is contraindicated in cases of renal and cardiac insufficiency and psychiatric problems and results in the development of complications and numerous side effects such as: confusion, difficulty concentrating, insomnia, loss of appetite, nausea and psychiatric problems (confusion, hallucinations, delirium syndrome, psychosis). In the last decade it has been demonstrated that other systems, such as the serotonergic system, are also involved, since in advanced stages of the disease L-DOPA is converted to dopamine in the serotonergic terminals and is released in an uncontrolled manner. However, compounds that act at this level, for example such as the serotonin 5-HT1a receptor agonists (buspirone, saritozan, tandospirone), may present problems, since although antidyskinetic effects were observed in preliminary trials, in certain cases they may affect the antiparkinsonian response. Or, for example, 5-HT1a/b agonists (eltoprazine and anpirtoline), which have a more favorable pharmacological profile than the former, but could also partially reduce the therapeutic effect of L-DOPA.

Thus, it is necessary to investigate and develop other prophylactic and/or therapeutic treatments for combating dyskinesias that have fewer side effects and are more effective.

BRIEF DESCRIPTION OF THE INVENTION

The results that are presented in this document demonstrate that inhibition of the RhoA/Rho kinase (ROCK) pathway makes it possible to treat and/or prevent the dyskinesias that may be caused by chronic treatment with L-DOPA, administered to patients with Parkinson's disease.

Thus, the present invention relates to a pharmaceutical composition that comprises a compound capable of inhibiting ROCK, for use in the prophylactic or therapeutic treatment of dyskinesias induced by L-DOPA.

The present invention further relates to pharmaceutical compositions of ROCK inhibitors, dosage forms thereof for different routes of administration and to certain doses useful for preventing dyskinesias, as well as to certain doses useful for treating dyskinesias.

DESCRIPTION OF THE FIGURES

FIG. 1A-FIG. 1F shows the effect of the dyskinesias induced by L-DOPA on the RhoA/ROCK pathway in the substantia nigra (FIG. 1A, FIG. 1B and FIG. 1C) and in the striatum (FIG. 1D, FIG. 1E and FIG. 1F). In dyskinetic animals treated with both doses of L-DOPA (6 mg/kg; LD-6 and 12 mg/kg) a significant increase was observed in protein expression for RhoA and ROCK (FIG. 1A, FIG. 1B) and activity for ROCK (C) in the substantia nigra, whereas in the striatum the differences were only significant with the high dose (FIG. 1D, FIG. 1E). However, after real-time PCR analysis, significant differences were observed with both doses in the striatum. The results were normalized with respect to the values for animals lesioned with 6-OHDA treated with saline. Data presented as mean value±SEM, t-Student*$p<0.05$ FIG. 2A FIG. 2A, FIG. 2C, FIG. 2E and FIG. 2G and 30-40 mg; FIG. 2B, FIG. 2D, FIG. 2F, FIG. 2H). In the group of animals co-treated with fasudil (white circles) a statistically significant reduction of these movements was observed both in the total score (FIG. 2A, FIG. 2B) and in the analysis of the separate components: extremity (FIG. 2C, FIG. 2D), axial (FIG. 2E, FIG. 2F), orolingual (FIG. 2G, FIG. 2H). Data presented as mean value±SEM (standard error of the mean), t-Student, *$p<0.05$ FIG. 3A

10 mg/kg (FIG. 3A), 30 and 40 mg/kg (FIG. 3B). The rotational behavior was also unaffected after the treatment with fasudil, indicating that the reduction of the dyskinesias is not due to a reduction of motor activity (FIG. 3C-FIG. 3E). Data presented as mean value±SEM, t-Student, *p<0.05

DETAILED DESCRIPTION OF THE INVENTION

As used in the description and the appended claims, the term "ROCK pathway" refers to the pathway in which the GTPase RhoA protein and its associated kinase (also known as Rho-kinase) participate. Rho A binds to a specific region of ROCK, activating it. ROCK phosphorylates various target proteins, including the light chain of myosin, reorganizing the actin of the cytoskeleton and regulating apoptic events (Amin E, Dubey B N, Zhang S C, Gremer L, Dvorsky R, Moll J M, Taha M S, Nagel-Steger L, Piekorz R P, Somlyo A V, Ahmadian M R (2013) Rho-kinase: regulation, (dys)function, and inhibition. Biol Chem 394:1399-410. doi: 10.1515/hsz-2013-0181.). This pathway is implicated in the inflammatory response in certain diseases, including neurodegenerative diseases such as Parkinson's disease. ROCK also acts in processes of autophagy, and inhibition of this pathway produces axonal stabilization, giving rise to neuroprotective effects. Two isoforms have been described, encoded by different genes: ROCK I and ROCK II. ROCK II is expressed preferentially in the brain (for a review see Labandeira-Garcia et al., 2014).

As used in the description and the appended claims, the term "compound capable of inhibiting the ROCK pathway" refers to a compound capable of reducing the activity of the enzyme and the expression levels thereof in a statistically significant manner relative to their corresponding controls to which the inhibitor was not administered. A person skilled in the art is able to test said inhibition by various methods, for example such as measurement of the activity of said ROCK enzyme by enzyme-immunoassay techniques (ROCK Activity Assay kit; Cell Biolabs, Inc., San Diego, Calif., USA) detecting the phosphorylation of myosin, the expression levels of mRNA by real-time PCR or the protein expression levels by Western blot. These techniques are described in detail in the following publication, which is incorporated in its entirety in the present description: Rodriguez-Perez A I, Dominguez-Meijide A, Lanciego J L, Guerra M J, Labandeira-Garcia J L. Inhibition of Rho kinase mediates the neuroprotective effects of estrogen in the MPTP model of Parkinson's disease. Neurobiol Dis. 2013 58:209-19. doi: 10.1016/j.nbd.2013.06.004

According to the present invention, a compound capable of inhibiting the ROCK pathway can regulate the ROCK pathway directly or indirectly.

As used in the description and the appended claims, the term "dyskinesias induced by L-DOPA" is to be understood as abnormal involuntary movements experienced by a mammal (for example a human being) having Parkinson's disease and being treated with L-DOPA.

In the present invention, the authors have investigated the effect produced at the molecular level by the chronic administration of L-DOPA in a rat model lesioned with 6-OHDA, demonstrating that the levels of Rho A and of ROCK increased relative to the control (see FIG. 1), which suggests an activation of this pathway. In these conditions, at the functional level the rats suffer from dyskinesias caused by chronic treatment with L-DOPA. On the basis of these experiments, a relation between activation of the ROCK pathway and dyskinesias is demonstrated for the first time. The present inventors have demonstrated that regulation of the ROCK pathway has an effect on dyskinesias, so that by inhibiting the ROCK pathway it is possible to reduce the dyskinesias already established in an animal model treated with L-DOPA (see example 4) or else reduce the development of dyskinesias in an animal model for which treatment with L-DOPA is beginning (see example 2).

Thus, in one aspect the invention relates to a pharmaceutical composition that comprises a compound capable of inhibiting the ROCK pathway, for use in the prophylactic or therapeutic treatment of dyskinesias induced by L-DOPA.

In a particular embodiment, the composition of the invention is administered in a dosage form suitable for intraperitoneal, oral or injectable administration. In a particular embodiment, injectable administration comprises intramuscular, subcutaneous, intravenous and intradermal administration.

In a particular embodiment, the ROCK inhibitor is selected from fasudil and derivatives thereof, Ripasudil, E-27632, E-32885, AMA-0076, AR-12286, AR-13324 (Rhopressa), KD-025 (Slx2119), LX7101, PG-324 (Roclatan), SAR407899.

In a preferred embodiment, an inhibitor of the ROCK pathway of interest for the present invention is fasudil. Accordingly, in a particular embodiment the invention relates to the pharmaceutical composition described above, where said compound is fasudil, a pharmaceutically acceptable salt thereof, or a derivative thereof. In another particular embodiment, the fasudil derivative is selected from hydroxy fasudil and dimethyl fasudil.

The present invention also describes that the administration of fasudil to a Parkinson animal model prior to being treated with L-DOPA, and moreover if during the treatment with L-DOPA fasudil is also administered, a preventive effect on dyskinesias is achieved, reducing their development throughout the treatment. In example 2, it is in addition demonstrated that in the case of acute administration of L-DOPA and when the dyskinesias are more pronounced, the treatment with fasudil is nevertheless effective, reducing the development of the dyskinesias compared to the case without treatment with fasudil (see example 2 and FIG. 2).

Thus, in a particular embodiment, the invention relates to the pharmaceutical composition of the invention for use in the prophylactic treatment of dyskinesias induced by L-DOPA that comprises: (i) the administration of said pharmaceutical composition in a therapeutically effective amount before the start of the treatment with L-DOPA, and (ii) the administration of a therapeutically effective amount of said pharmaceutical composition simultaneously with or sequentially to each administration of L-DOPA.

In a particular embodiment, the invention relates to a method for preventing dyskinesias induced by L-DOPA, where the patient has Parkinson's disease, the method comprises administering a therapeutically effective amount of fasudil prior to the start of the treatment with L-DOPA, and administering a therapeutically effective amount of fasudil simultaneously with or sequentially to each administration of L-DOPA.

In a particular embodiment, the invention relates to a pharmaceutical composition of the invention for use in a prophylactic treatment of dyskinesias induced by L-DOPA.

In this case, moreover, there is an additional advantage since at this dose, fasudil provides neuroprotection for patients with Parkinson's disease and slows down dopaminergic degeneration (Villar-Cheda B, Dominguez-Meijide A, Joglar B, Rodriguez-Perez A I, Guerra M J, Labandeira-Garcia J L. (2012) Involvement of microglial RhoA/Rho-kinase pathway activation in the dopaminergic neuron death. Role of angiotensin via angiotensin type 1 receptors. Neurobiol Dis 47: 268-79 doi: 10.1016/j.nbd.2012.04.010). Furthermore, administration of the composition of the invention for preventing dyskinesias has a preferred posology as described above that also promotes the neuroprotective effect of fasudil (Borrajo A, Rodriguez-Perez A I, Villar-Cheda B, Guerra M J, Labandeira-Garcia J L. (2014) Inhibition of the microglial response is essential for the neuroprotective effects of Rho-kinase inhibitors on MPTP-induced dopaminergic cell death. Neuropharmacology 85: 1-8 doi: 10.1016/j.neuropharm.2014.05.021; Villar-Cheda B, Dominguez-Meijide A, Joglar B, Rodriguez-Perez A I, Guerra M J, Labandeira-Garcia J L. (2012) Involvement of microglial RhoA/Rho-kinase pathway activation in the dopaminergic neuron death. Role of angiotensin via angiotensin type 1 receptors. Neurobiol Dis 47: 268-79 doi: 10.1016/j.nbd.2012.04.010; Labandeira-Garcia J L, Rodriguez-Perez A I, Villar-Cheda B, Borrajo A, Dominguez-Meijide A, Guerra M J. (2015) Rho Kinase and Dopaminergic Degeneration: A Promising Therapeutic Target for Parkinson's Disease. Neuroscientist 21: 616-29 doi: 10.1177/1073858414554954).

The present invention also describes the usefulness of the compositions of the present invention for the therapeutic treatment of dyskinesias induced by L-DOPA. In example 4 it is demonstrated that even in cases where the dyskinesias are already established, the composition with a ROCK inhibitor is capable of reducing them. By increasing the dose of fasudil (40 mg/kg), the dyskinesias are reduced almost to 50% in those animals that are already dyskinetic (treated periodically with L-DOPA for 3-4 weeks). Even when after acute administration of L-DOPA the dyskinesias are more reduced when it is accompanied by administration of the compositions of the invention.

Thus, in a particular embodiment, the invention relates to the pharmaceutical composition of the invention for use in the therapeutic treatment of dyskinesias induced by L-DOPA that comprises the administration of a therapeutically effective amount of said pharmaceutical composition simultaneously with or sequentially to each administration of L-DOPA.

In a particular embodiment, the invention relates to a method for treating dyskinesias induced by L-DOPA, where the patient has Parkinson's disease, the method comprises administering a therapeutically effective amount of fasudil simultaneously with or sequentially to each administration of L-DOPA.

In a particular embodiment, the invention relates to a pharmaceutical composition of the invention for use in a therapeutic treatment of dyskinesias induced by L-DOPA.

One of the preferred routes of administration in the present invention is injectable, and thus in a particular embodiment of the invention it relates to the pharmaceutical composition as has been described above, whose dosage form is suitable for injectable administration for use in the prevention or treatment of dyskinesias induced by L-DOPA.

Another preferred route of administration in the present invention is the oral route, and thus in a particular embodiment of the invention it relates to the pharmaceutical composition as has been described above, whose dosage form is suitable for oral administration for use in the prevention or treatment of dyskinesias induced by L-DOPA.

The following examples serve to illustrate the present invention and do not represent a limitation thereof.

Methods and Experimental Design

In the following examples, rats of the Sprague-Dawley strain were used, which were injected with the neurotoxin 6-hydroxydopamine (6-OHDA) in accordance with stereotaxic techniques in the medial forebrain bundle. This technique is one of the most widely laboratory models for studying Parkinson's disease (PD) and its possible treatment pathways (Ungerstedt U. 6-Hydroxy-dopamine induced degeneration of central monoamine neurons. Eur J Pharmacol. (1968) 5(1): 107-10; Cenci M A, Crossman A R. Animal models of l-dopa-induced dyskinesia in Parkinson's disease. Mov Disord (2018) 33(6):889-899. doi: 10.1002/mds.27337).

To establish an animal model of dyskinesias, the animals were treated chronically with L-DOPA 6 mg/kg (therapeutic dose) and benserazide (10 mg/kg) for 3-4 weeks and during this period the abnormal involuntary movements (AIMs) were evaluated with a special test (Cenci M A, Lundblad M. Ratings of L-DOPA-induced dyskinesia in the unilateral 6-OHDA lesion model of Parkinson's disease in rats and mice. Curr Protoc Neurosci. (2007) Chapter 9: Unit 9.25. doi: 10.1002/0471142301).

Example 1

Investigation of the Dyskinetic Model

A group of animal models of PD was injected daily with different doses of L-DOPA (6 mg/kg and 12 mg/kg), until the levels of dyskinesia were stable (3-4 weeks). At autopsy, the striatum and the substantia nigra were dissected and the expression levels of RhoA and ROCK were analyzed by Western blot and real-time PCR.

It was observed that in the dyskinetic animals there was a significant increase in the levels of the RhoA protein and of the ROCK protein. It was also observed that in the animals treated with the higher dose of L-DOPA, and which showed earlier and more severe dyskinesias, the increase in the levels of said proteins was greater (see FIG. 1).

This experiment demonstrates that the ROCK pathway is activated in dyskinetic animals.

Example 2

Treatment with Fasudil During Chronic Treatment with L-DOPA

A group of rats treated with L-DOPA as described above was used as the control in this study. In addition to L-DOPA, an inhibitor of the ROCK pathway, fasudil, was administered to one group at a dose of 10 mg/kg/day, by the intraperitoneal route (although it could be administered by the oral route after suitably adjusting the dose), beginning 5 days before starting the treatment with L-DOPA, and 30 minutes before each administration of L-DOPA. In addition to L-DOPA, another group was administered fasudil at a dose of 30 and 40 mg/kg/day, intraperitoneally with the same frequency as the preceding group. In all cases, the treatment was carried out chronically for 3 weeks, and the abnormal involuntary movements were evaluated during this period.

In the animals treated with a low dose of fasudil (10 mg/kg) and L-DOPA, a statistically significant reduction was observed in the development of dyskinesias relative to the group of animals treated only with L-DOPA: approximately a 25% reduction in dyskinesias in the extremities, a 30% orolingual reduction and a 35% axial reduction. The reduction of dyskinesias was observed starting from the 5th day.

When the dose of fasudil was increased (30 mg/kg), a greater reduction in dyskinesias was observed in all the dyskinetic components analyzed (70% orolingual, 60% axial and 60% extremity). On increasing the fasudil dose to 40 mg/kg, the reduction in dyskinesia reached 70%.

At the end of the treatment the dose of L-DOPA was increased to 24 mg/kg to verify whether fasudil is also effective in conditions of severe dyskinesia, a significant large reduction being observed, of approximately 50% (see FIG. 2).

This study demonstrates that an inhibitor of the ROCK pathway, such as fasudil, is useful for reducing the development of dyskinesias, even when these are caused by acute doses of L-DOPA.

Example 3

Figure 1A:
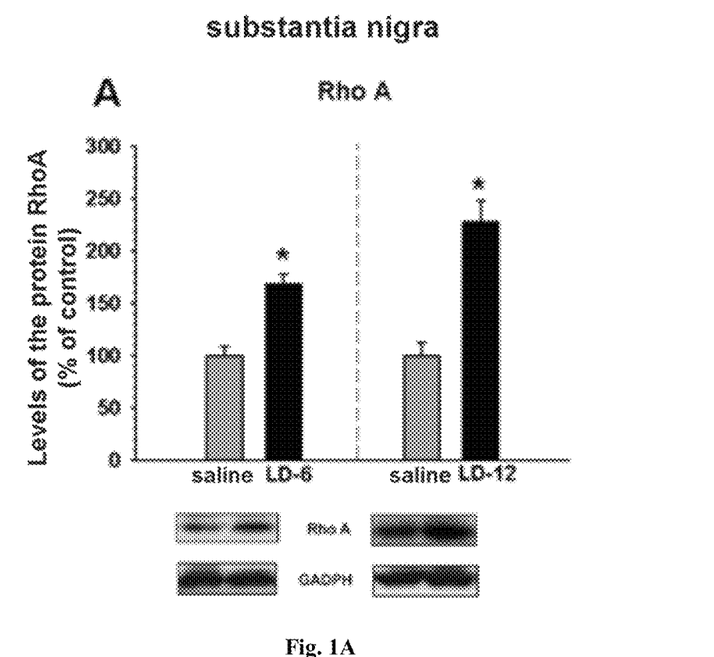
Figure 1B:
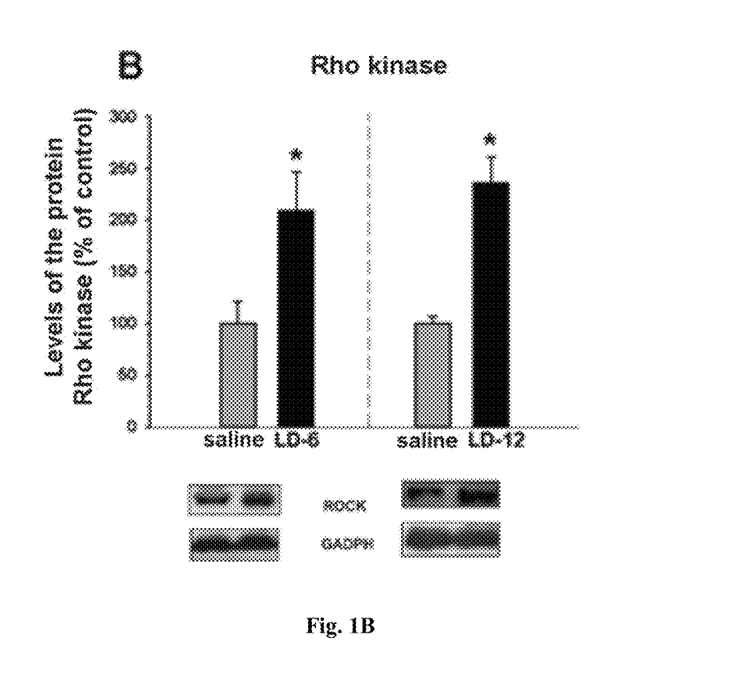
Figure 1C:
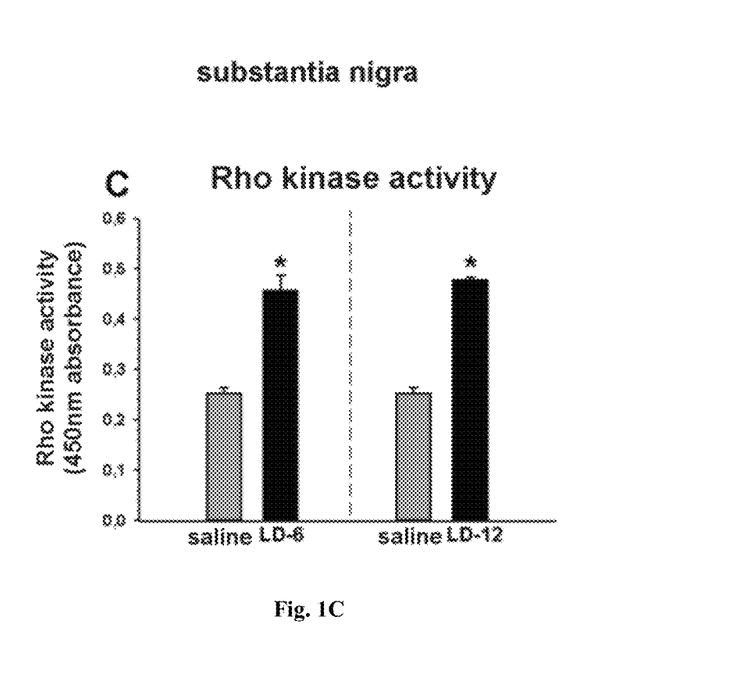
Figure 1D:
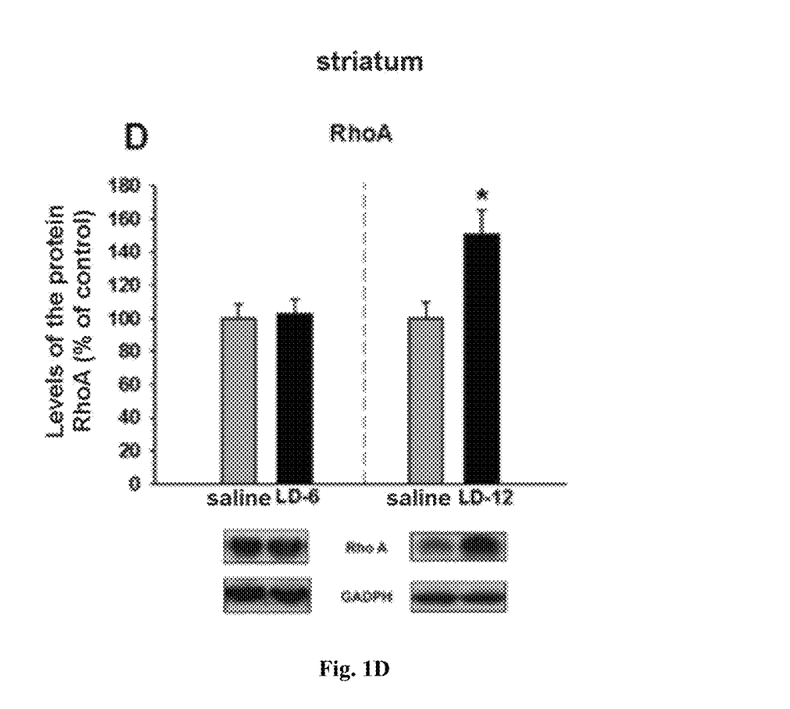
Figure 1E:
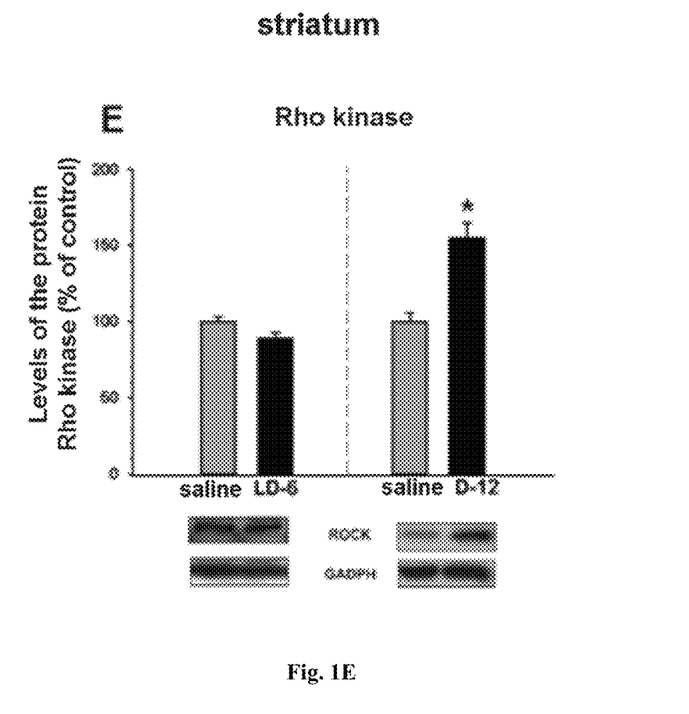
Figure 1F:
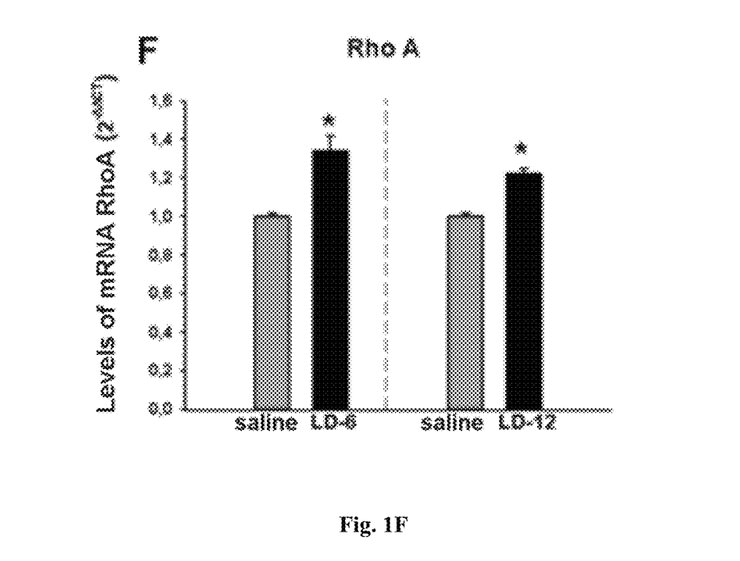
Figure 2A:
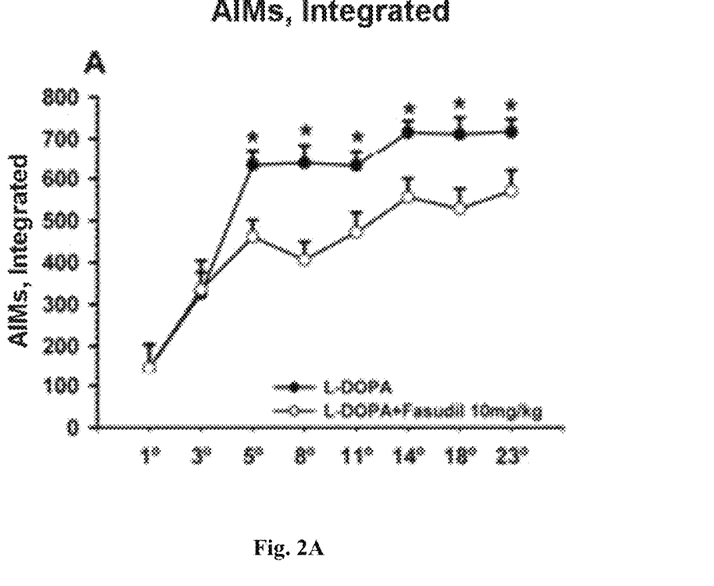
Figure 2B:
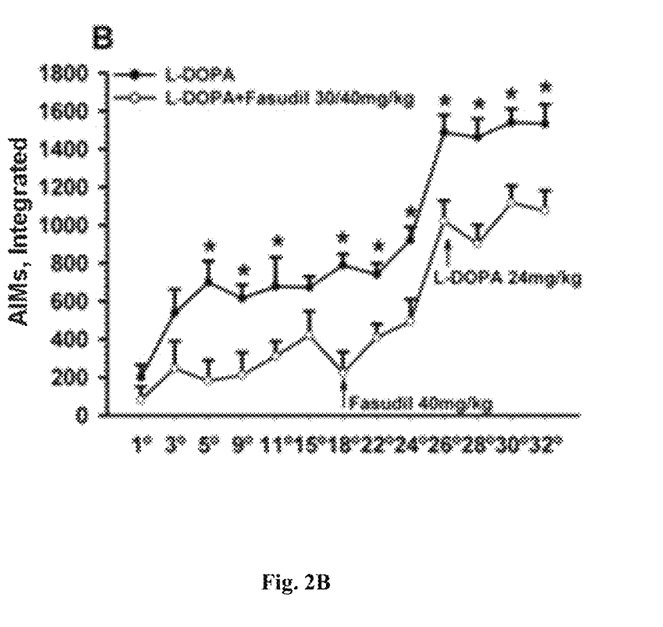
Figure 2C:
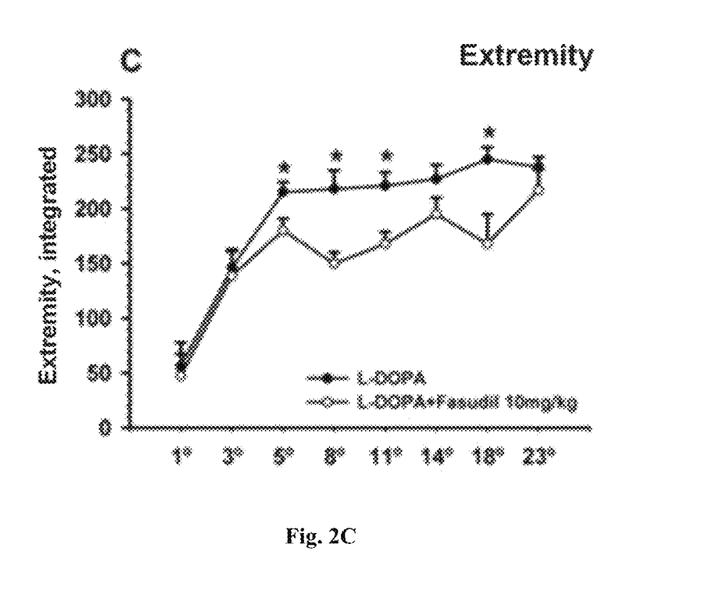
Figure 2D:
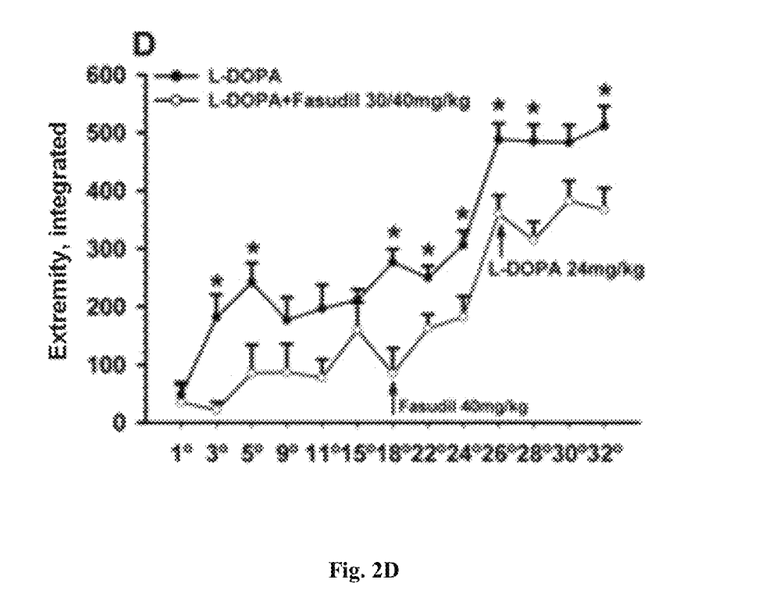
Figure 2E:
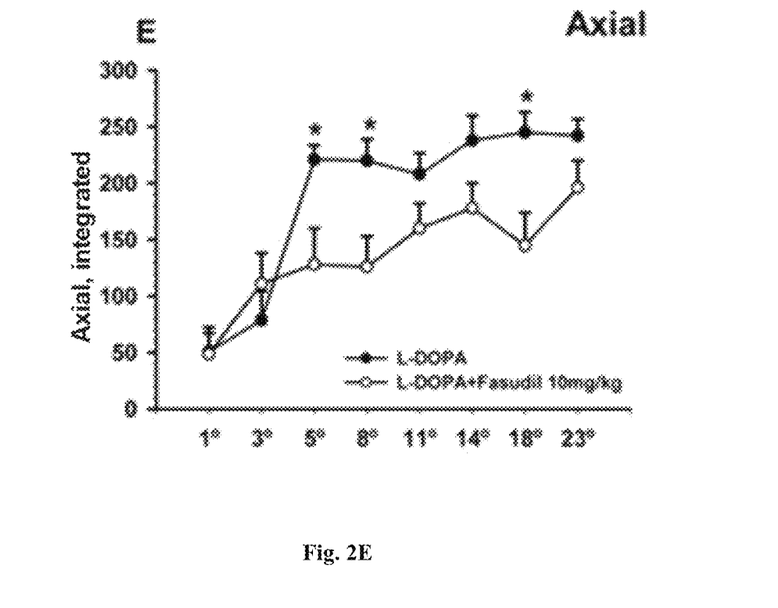
Figure 2F:
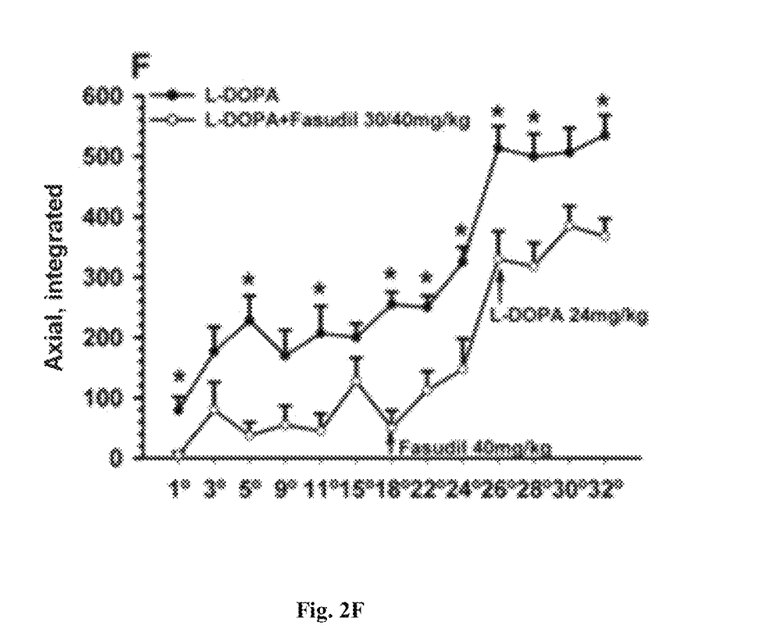
Figure 2G:
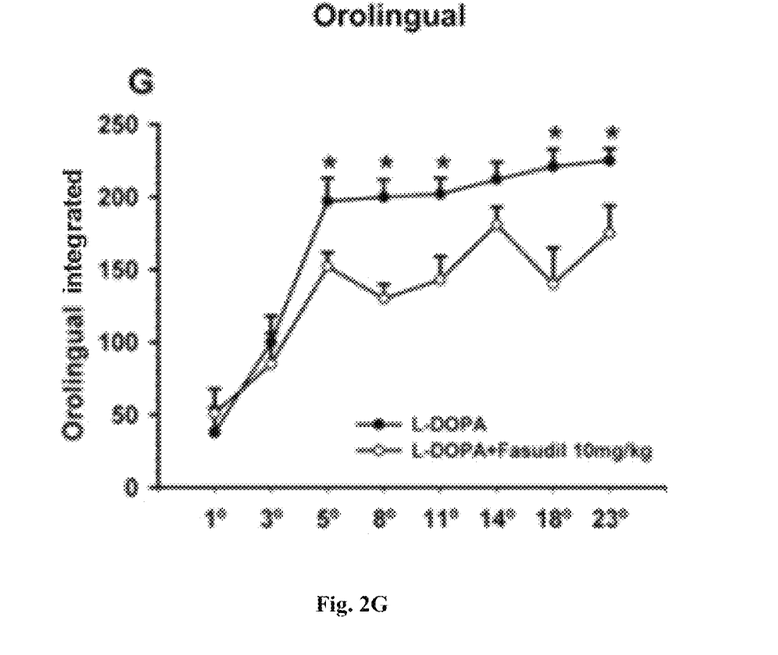
Figure 2H:
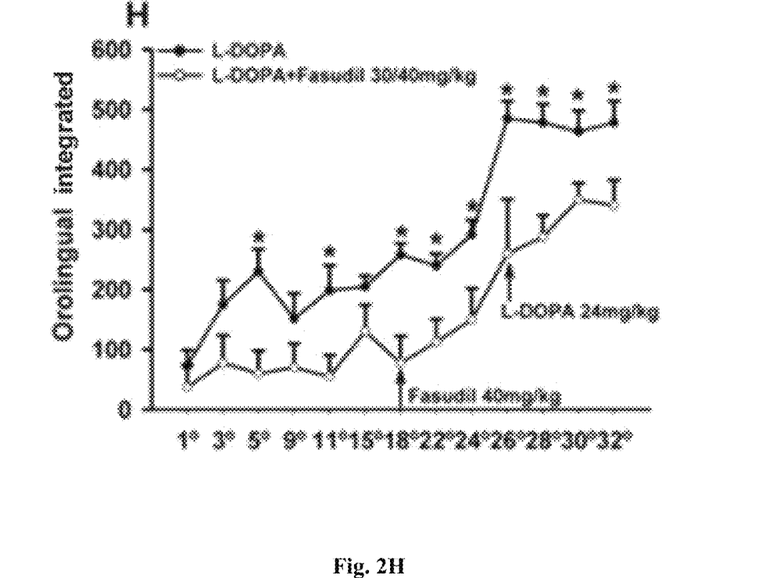
-FIG. 2H shows the abnormal involuntary movements (AIMs) observed after chronic treatment with L-DOPA (23 and 32 days) and different doses of fasudil (10 mg/kg.
Figure 3A:
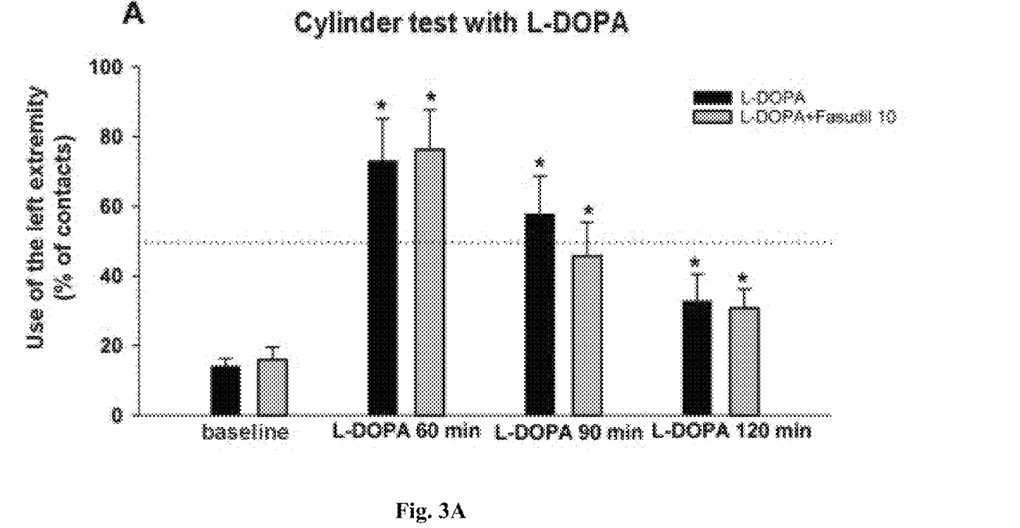
Figure 3B:
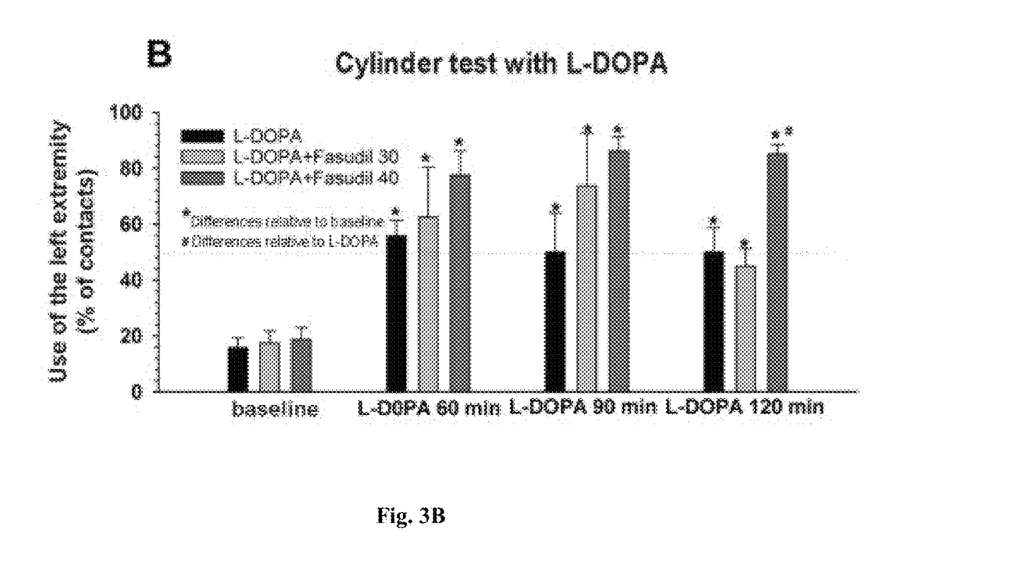
Figure 3C:
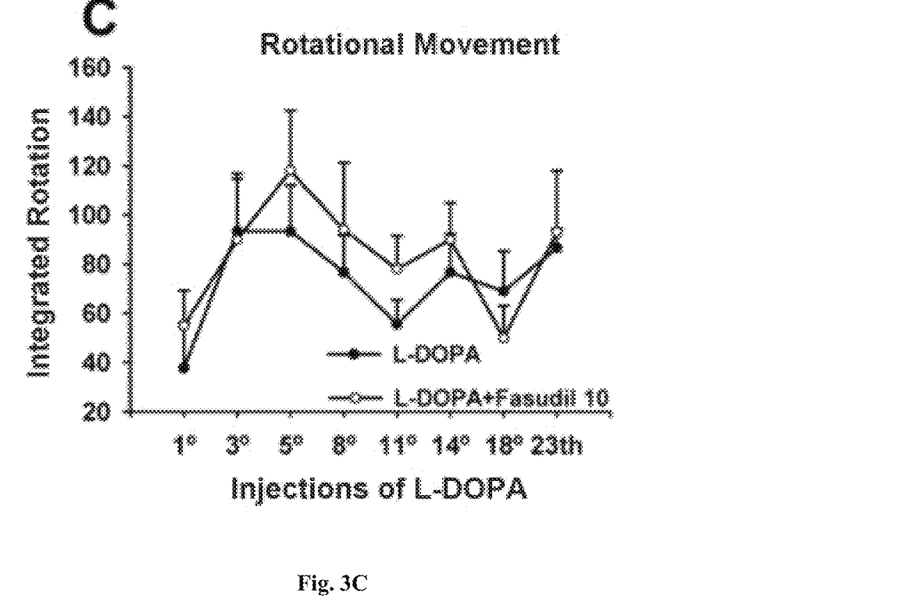
Figure 3D:
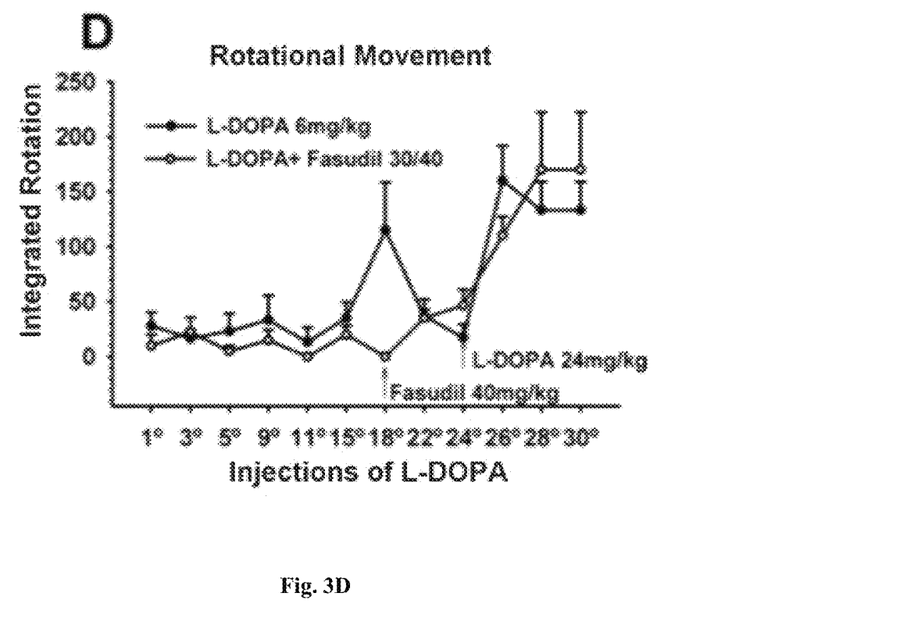
Figure 3E:
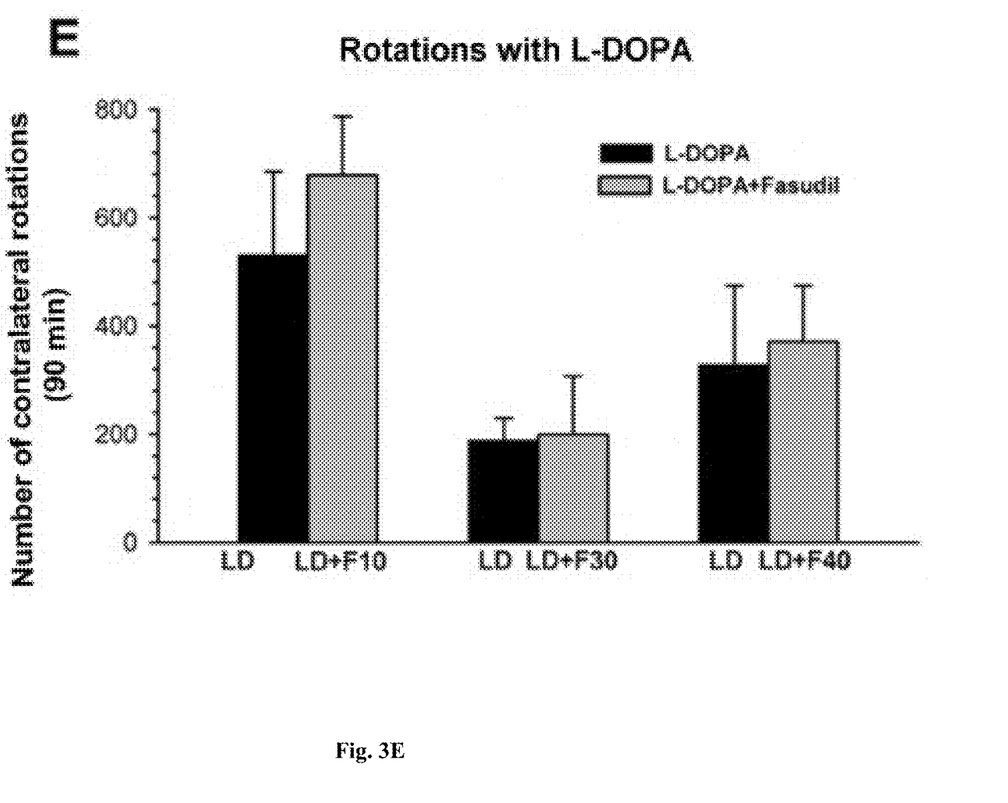
-FIG. 3E shows the cylinder test in animals with unilateral dopaminergic lesion, where <20% of the use of the left extremity is observed in baseline conditions, and recovery of the motor asymmetry after injection of L-DOPA at 60 and 90 min in the control animals (only L-DOPA; black bars) and in those animals co-treated with fasudil (gray bars)

Study of the Interaction Between Inhibition of the ROCK Pathway and the Therapeutic Effect of L-DOPA To investigate whether fasudil could interfere with the therapeutic effect of L-DOPA, the cylinder test was carried out, which is based on analysis of the motor asymmetry affecting the animals after unilateral lesion with 6-OHDA (Schallert T, Kozlowski D A, Humm J L, Cocke R R. (1997) 73:229-38). In this experiment the animals treated with fasudil at all the doses studied (10, 30 and 40 mg/kg) recovered the motor asymmetry caused by the lesion 1 h after injection of L-DOPA, no differences being observed relative to the animals injected only with L-DOPA, indicating that this compound does not alter the therapeutic effect of L-DOPA (see FIG. 3A-B). Moreover, in experiments in which the rotational behavior was evaluated, no differences were observed in the rotations induced by L-DOPA in the animals treated with the different doses of fasudil, demonstrating that the reduction in dyskinesias is not due to a reduction in motor activity (see FIG. 3C-E).

This experiment demonstrates that inhibition of the ROCK pathway, by the administration of fasudil, even at high doses, does not interfere with the therapeutic effect of L-DOPA.

Example 4

Investigation of the Therapeutic Effect

A group of animals with unilateral lesion with 6-OHDA were treated daily with L-DOPA for 3 weeks and then they were treated with L-DOPA and fasudil to investigate whether inhibition of the ROCK pathway allows dyskinesias to be reduced once they are already established.

When a fasudil dose of 10 mg/kg/day was used, no improvement in the animals was observed (up to 7 days of treatment).

However, when a fasudil dose of 40 mg/kg/day was used, there was a reduction in dyskinesias of about 45% starting from the third day of treatment.

Figure 4A:
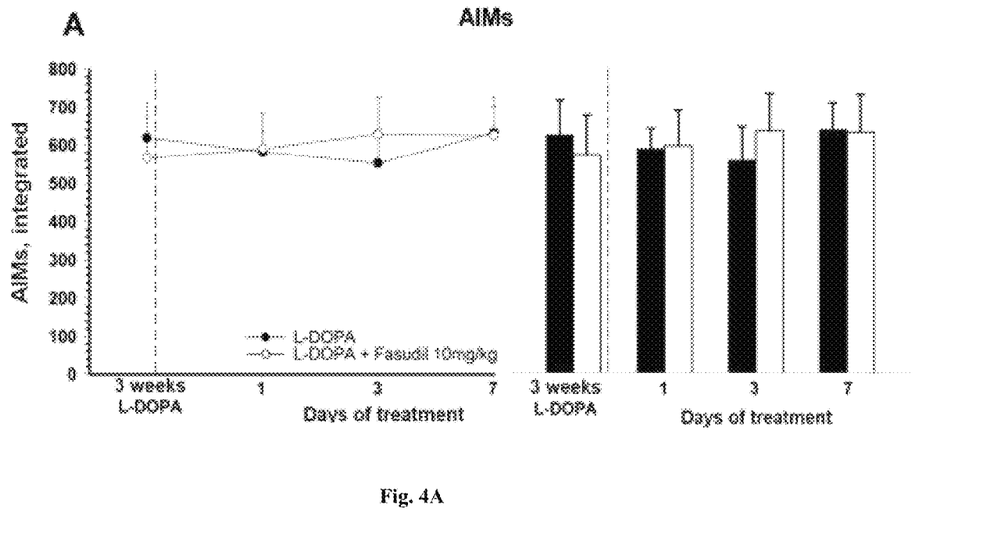
FIG. 4A-FIG. 4B shows the effect of ROCK inhibition in animals with a stable degree of dyskinesia (chronic treatment with L-DOPA, 3 weeks). In this case, fasudil at the low dose (10 mg/kg, A) did not have any effect on the dyskinetic movements (FIG. 4A). However, high doses of the compound (30 and 40 mg/kg) gave rise to a significant reduction of L-DOPA even with the high dose of L-DOPA (24 mg/kg) (FIG. 4B). Data presented as mean value±SEM, t-Student*p<0.05
Figure 4B:
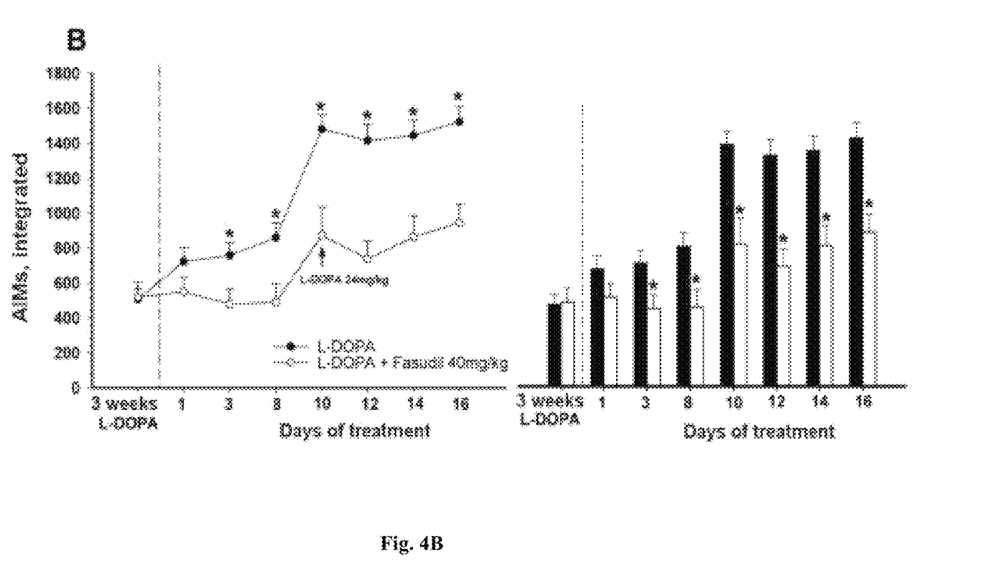

On increasing the dose of L-DOPA to 24 mg/kg, causing a condition of severe dyskinesia, the reduction was even greater, approximately 50%, which was maintained up to the end of the treatment (see FIG. 4).

The invention claimed is:

1. A method for the prevention or treatment of dyskinesias induced by L-DOPA comprising administering to a subject in need thereof a pharmaceutical composition comprising a compound that inhibits RhoA/Rho kinase (ROCK) pathway.

2. The method according to claim 1, wherein the compound is selected from the group consisting of Fasudil, Ripasudil, E-27632, E-32885, AMA-0076, AR-12286, AR-13324 (Rhopressa), KD-025 (Slx2119), LX7101, PG-324 (Roclatan), and SAR407899.

3. The method according to claim 1, wherein the compound is Fasudil, a pharmaceutically acceptable salt thereof, or an analog thereof.

4. The method according to claim 1, wherein the composition is administered in a dosage form suitable for oral or injectable administration.

5. The method according to claim 1, wherein the compound is Fasudil or a pharmaceutically acceptable salt thereof whose dosage form is suitable for oral or injectable administration and is for the prevention of dyskinesias induced by L-DOPA.

6. The method according to claim 1, wherein the administration of the pharmaceutical composition in a therapeutically effective amount occurs before the start of the treatment with L-DOPA, or wherein the administration of a therapeutically effective amount of the pharmaceutical composition occurs simultaneously with or sequentially to each administration of L-DOPA.

7. The method according to claim 6, wherein the compound is Fasudil or a pharmaceutically acceptable salt thereof whose dosage form is suitable for oral or injectable administration.

8. The method according to claim 1, wherein administration of a therapeutically effective amount of said pharmaceutical composition simultaneously with or sequentially to each administration of L-DOPA.

9. The method according to claim 8, wherein the compound is Fasudil or a pharmaceutically acceptable salt thereof whose dosage form is suitable for oral or injectable administration.

10. The method according to claim 1, wherein the compound is Fasudil or a pharmaceutically acceptable salt thereof whose dosage form is suitable for oral or injectable administration and is for the treatment of dyskinesias induced by L-DOPA.

11. The method according to claim 1, wherein the dyskinesia is a peak-dose dyskinesia.

12. The method according to claim 1, wherein the dyskinesia is a diphasic dyskinesia.

13. The method according to claim 1, wherein the dyskinesia is an off-period dystonia.

* * * * *

UNITED STATES PATENT AND TRADEMARK OFFICE
CERTIFICATE OF CORRECTION

| | |
|---|---|
| PATENT NO. | : 11,337,985 B2 |
| APPLICATION NO. | : 17/406689 |
| DATED | : May 24, 2022 |
| INVENTOR(S) | : Ana M. Munoz Patino, Jose Luis Labandeira Garcia and Andrea Lopez Lopez |

It is certified that error appears in the above-identified patent and that said Letters Patent is hereby corrected as shown below:

In the Specification

At Column 4, Line 30 please delete the following:
"E-27632, E-32885, AMA-0076, AR-12286, AR-13324"
And insert:
-- Y-27632, Y-32885, AMA-0076, AR-12286, AR-13324 --

In the Claims

In Claim 2 at Column 8, Line 20 please delete the following:
"Ripasudil, E-27632, E-32885, AMA-0076, AR12286,"
And insert:
-- Ripasudil, Y-27632, Y-32885, AMA-0076, AR12286, --

Signed and Sealed this
Eighth Day of August, 2023

Katherine Kelly Vidal
*Director of the United States Patent and Trademark Office*